(12) United States Patent
Davis et al.

(10) Patent No.: US 9,464,047 B2
(45) Date of Patent: Oct. 11, 2016

(54) PROCESS FOR CONCENTRATING A MIXTURE CONTAINING ORGANIC HYDROPEROXIDE

(71) Applicant: ExxonMobil Chemical Patents Inc., Baytown, TX (US)

(72) Inventors: Jason D. Davis, Beaumont, TX (US); Christopher L. Becker, Manhattan, KS (US); Travis A. Reine, Slidell, LA (US); Bryan A. Patel, Jersey City, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/893,003

(22) PCT Filed: Jun. 6, 2014

(86) PCT No.: PCT/US2014/041410
§ 371 (c)(1),
(2) Date: Nov. 20, 2015

(87) PCT Pub. No.: WO2014/209578
PCT Pub. Date: Dec. 31, 2014

(65) Prior Publication Data
US 2016/0122298 A1 May 5, 2016

Related U.S. Application Data

(60) Provisional application No. 61/841,072, filed on Jun. 28, 2013.

(30) Foreign Application Priority Data

Sep. 11, 2013 (EP) ..................... 13183958

(51) Int. Cl.
| | | |
|---|---|---|
| C07C 45/53 | (2006.01) | |
| C07C 37/08 | (2006.01) | |
| C07C 407/00 | (2006.01) | |
| C07C 29/132 | (2006.01) | |

(52) U.S. Cl.
CPC ........... *C07C 407/00* (2013.01); *C07C 29/132* (2013.01); *C07C 37/08* (2013.01); *C07C 45/53* (2013.01); *C07C 407/003* (2013.01); *C07C 2101/14* (2013.01)

(58) Field of Classification Search
CPC ...... C07C 45/53; C07C 37/08; C07C 407/00
USPC ................................. 568/342, 347, 798, 570
See application file for complete search history.

(56) References Cited

U.S. PATENT DOCUMENTS 4,654,124 A    3/1987 Elias et al.

FOREIGN PATENT DOCUMENTS

| GB | 740 022 | 11/1955 |
| GB | 842 586 | 7/1960 |
| WO | 2010/074779 | 7/2010 |

*Primary Examiner* — Sikarl Witherspoon
(74) *Attorney, Agent, or Firm* — Siwen Chen

(57) ABSTRACT

Method for concentrating an organic hydroperoxide mixture comprising a hydrocarbon and a hydroperoxide corresponding thereto comprises evaporating a first liquid mixture in a thin-film evaporation device followed by separation in a separation zone. Both the evaporation device and the separation zone operate at a low absolute pressure at a temperature lower than the thermal degradation temperature of the hydroperoxide to prevent thermal decomposition thereof. The process is particularly useful for concentrating an oxidation product made from the oxidation of cyclohexylbenzene.

24 Claims, 1 Drawing Sheet

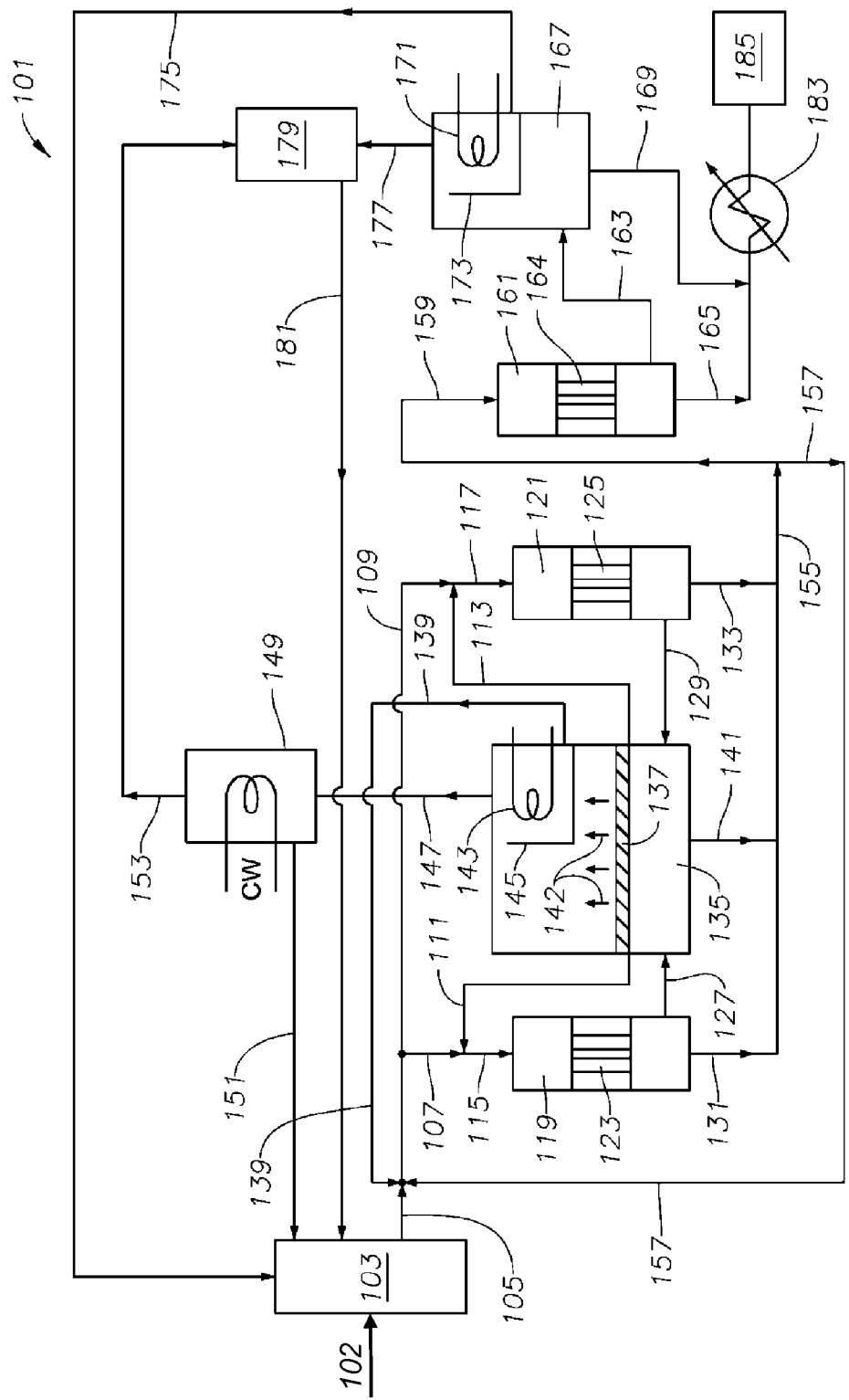

under the pressure conditions at the pressure-reducing valve (101), cyclohexylbenzene was recirculated to the hydroperoxide concentrator.

PROCESS FOR CONCENTRATING A MIXTURE CONTAINING ORGANIC HYDROPEROXIDE

PRIORITY CLAIM

This application is a National Stage Application of International Application No. PCT/US2014/041410 filed Jun. 6, 2014, which claims priority to U.S. Provisional Application Ser. No. 61/841,072 filed Jun. 28, 2013, and European Application No. 13183958.1 filed Sep. 11, 2013, the disclosures of which are fully incorporated herein by their reference.

FIELD

The present invention relates to processes for increasing the concentration of an organic hydroperoxide in an organic dispersion comprising a hydrocarbon and a hydroperoxide thereof. In particular, the present invention relates to processes for increasing the concentration of cyclohexylbenzene hydroperoxide in mixture containing cyclohexylbenzene hydroperoxide and cyclohexylbenzene. The present invention is useful, e.g., in producing cyclohexanone and phenol from the oxidation of cyclohexylbenzene.

BACKGROUND

Phenol is an important product in the chemical industry and is useful in, for example, the production of phenolic resins, bisphenol A, ε-caprolactam, adipic acid, plasticizers, and polymers such as nylon-6.

Currently, a common route for the production of phenol is the three-step Hock process via cumene. This first step of this process involves alkylation of benzene with propylene in the presence of an acidic catalyst to produce cumene. The second step is oxidation, preferably aerobic oxidation, of cumene to the corresponding cumene hydroperoxide. The third step is the cleavage of the cumene hydroperoxide in the presence of heterogeneous or homogeneous catalysts into equimolar amounts of phenol and acetone, a co-product. However, the world demand for phenol is growing more rapidly than that for the acetone co-product. In addition, the cost of propylene is generally high.

Thus, a process that avoids or reduces the use of propylene as a feed and coproduces higher ketones, rather than acetone, may be an attractive alternative route to the production of phenol. In addition, there is a growing market for cyclohexanone, which is used as an industrial solvent, as an activator in oxidation reactions and in the production of adipic acid, cyclohexanone resins, cyclohexanone oxime, caprolactam, and nylon-6.

Phenol and cyclohexanone can be co-produced by a variation of the Hock process in which cyclohexylbenzene is oxidized to obtain cyclohexylbenzene hydroperoxide, which, in turn, is decomposed in the presence of an acid catalyst to the desired phenol and cyclohexanone in a process termed "cleavage."

WO 2010/074779 discloses that cyclohexylbenzene hydroperoxide can be produced by aerobic oxidation of cyclohexylbenzene in the presence of a catalyst. Due to reaction condition constraints, the oxidation product normally comprises a significant amount of cyclohexylbenzene. It has been found that in the cleavage reaction of cyclohexylbenzene hydroperoxide, a relatively low concentration of cyclohexylbenzene in the reaction medium is conducive to reduced side reactions, hence higher yield of desired products, i.e., cyclohexanone and phenol. This calls for the removal of cyclohexylbenzene from the oxidation product. Given the high boiling points of cyclohexylbenzene and cyclohexylbenzene hydroperoxide, and the thermal instability of cyclohexylbenzene hydroperoxide, concentrating a cyclohexylbenzene hydroperoxide mixture is not an easy undertaking.

SUMMARY

The present disclosure provides a means for removing cyclohexylbenzene from a mixture containing cyclohexylbenzene and cyclohexylbenzene hydroperoxide to obtain a cyclohexylbenzene hydroperoxide product with a desired concentration thereof.

Thus, a first aspect of the present disclosure relates to a process for making a cyclohexylbenzene hydroperoxide product, the process comprising:

(I) providing a first liquid mixture comprising cyclohexylbenzene and cyclohexylbenzene hydroperoxide;

(II) forming a second vapor/liquid mixture stream and a second liquid stream by passing the first liquid mixture through a first thin-film evaporation device under a first absolute pressure of at most 80 kPa;

(III) separating the second vapor/liquid mixture stream in a first separation zone under a second absolute pressure of at most 80 kPa to obtain a third liquid stream and a third vapor stream;

(IV) condensing a part of the third vapor stream to obtain a fourth liquid stream and a fourth vapor stream;

(V) recycling at least a part of the fourth liquid stream to the first separation zone; and (VI) obtaining the cyclohexylbenzene hydroperoxide product from the third liquid stream and/or the second liquid stream, wherein the cyclohexylbenzene hydroperoxide product has a higher concentration of cyclohexylbenzene hydroperoxide compared to the first liquid mixture.

A second aspect of the present disclosure relates to a process for making an organic hydroperoxide product, the process comprising:

(2I) providing a first liquid mixture comprising a hydrocarbon and a hydroperoxide corresponding to the hydrocarbon;

(2II) forming a second vapor/liquid mixture stream and a second liquid stream by passing the first liquid mixture through a first thin-film evaporation device under a first absolute pressure of at most 80 kPa;

(2III) separating the second vapor/liquid mixture stream in a first separation zone under a second absolute pressure of at most 80 kPa to obtain a third liquid stream and a third vapor stream;

(2IV) condensing a part of the third vapor stream at a location inside the first separation zone to obtain a fourth liquid stream and a fourth vapor stream;

(2V) recycling at least a part of the fourth liquid stream to the first separation zone;

(2VI) condensing a part of the fourth vapor stream at a location outside of the first separation zone to obtain a fifth liquid stream and a fifth vapor stream;

(2VII) obtaining the organic hydroperoxide product from the third liquid stream and/or the second liquid stream, wherein the organic hydroperoxide product has a higher concentration of the hydroperoxide compared to the first liquid mixture.

A third aspect of the present disclosure relates to an apparatus for making a cyclohexylbenzene hydroperoxide product, comprising:

(A1) at least one first thin-film evaporation device capable of receiving a first liquid mixture comprising cyclohexylbenzene and cyclohexylbenzene hydroperoxide and operating under an absolute pressure of not higher than 80 kPa to generate a second vapor/liquid mixture stream and a second liquid stream;

(A2) a first separation device in fluid communication with the first thin-film evaporator capable of separating the second vapor/liquid mixture stream into a third vapor stream and a third liquid stream;

(A3) a first condenser capable of condensing a part of the third liquid stream to obtain a fourth liquid stream and a fourth vapor stream;

(A4) a fluid conduit capable of delivering a part of the fourth liquid stream to the first thin-film evaporation device; and (A5) a vacuum pump in fluid communication with the first separation device capable of generating an absolute pressure of at most 80 kPa inside the first separation device.

A fourth aspect of the present disclosure relates to an apparatus for making phenol and/or cyclohexanone, comprising:

(B1) an apparatus of the second aspect; and (B2) a cleavage reactor receiving at least a portion of the second liquid stream and/or the third liquid stream and/or the sixth liquid stream, and capable of allowing a cleavage reaction of cyclohexylbenzene hydroperoxide to obtain a cleavage effluent comprising phenol and cyclohexanone.

A fifth aspect of the present disclosure relates to an apparatus for making an organic hydroperoxide product, comprising:

(C1) at least one first thin-film evaporation device capable of receiving a first liquid mixture comprising a hydrocarbon and a hydroperoxide corresponding to the hydrocarbon and operating under an absolute pressure of not higher than 80 kPa to generate a second vapor/liquid mixture stream and a second liquid stream;

(C2) a first separation device in fluid communication with the first thin-film evaporator capable of separating the second vapor/liquid mixture stream into a third vapor stream and a third liquid stream;

(C3) a first condenser located inside the first separation device capable of condensing a part of the third liquid stream to obtain a fourth liquid stream and a fourth vapor stream;

(C4) a fluid conduit capable of delivering a part of the fourth liquid stream to the first thin-film evaporation device;

(C5) a second condenser located outside of the first separation device in fluid communication with the first condenser capable of condensing a part of the fourth vapor stream to obtain a fifth vapor stream and a fifth liquid stream; and (C6) a vacuum pump in fluid communication with the first separation device capable of generating an absolute pressure of at most 80 kPa inside the first separation device.

BRIEF DESCRIPTION OF THE DRAWINGS

FIG. 1 is a schematic illustration of an exemplary process according to the present disclosure for making a concentrated cyclohexylbenzene hydroperoxide product starting from the oxidation of cyclohexylbenzene.

DETAILED DESCRIPTION

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other steps, or in any other order, as the case may be. In addition, one or more or even all steps may be conducted simultaneously with regard to the same or different batch(es) of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a catalyst" include embodiments where one, two, or more different types of the catalyst are used, unless specified to the contrary or the context clearly indicates that only one type of the catalyst is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene.

As used herein, the generic term "cyclohexylbenzene hydroperoxide" includes all isomers of cyclohexylbenzene hydroperoxide, the formulas of which are indicated below:

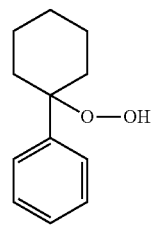

(F-I)

phenyl-1-cyclohexyl-1-hydroperoxide

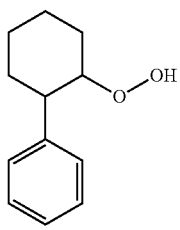

phenyl-1-cyclohexyl-2-hydroperoxide

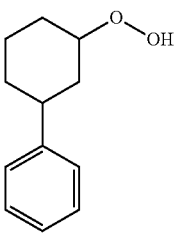

phenyl-1-cyclohexyl-3-hydroperoxide

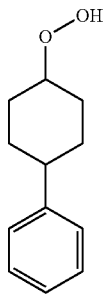

phenyl-1-cyclohexyl-4-hydroperoxide

Thus, in the present disclosure, a mixture comprising cyclohexylbenzene hydroperoxide may comprise one or more of the isomers with the above formulas (F-I), (F-II), (F-III) and (F-IV). Of particular interest in the present disclosure is a product comprising primarily the isomer with formula (F-I), i.e., phenyl-1-cyclohexyl-1-hydroperoxide, which can undergoes the following reaction in the presence of an acid catalyst:

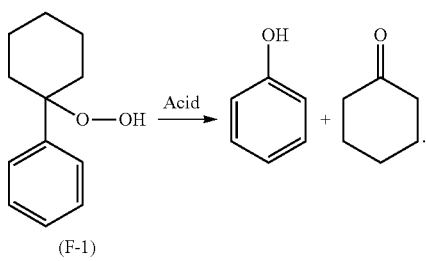

However, it is expected that the invention in the present disclosure can be equally useful for the production of isomers having formulas (F-II), (F-III), and (F-IV). It should be understood that in a product comprising primarily one of the isomers (F-I), (F-II), (F-III) and (F-IV), a small amount of one or more other isomers may be present due to the method of making the particularly interested isomer, such as the one with formula (F-I) above.

As used herein, the term "thermal degradation temperature" of an organic hydroperoxide is the lowest temperature at which a given quantity of the pure organic hydroperoxide material decomposes in 101 kPa air at a rate of at least 10% in 10 minutes.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one, or more than one, unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

The Organic Hydroperoxide Concentration Process

A first aspect of the present disclosure relates to a process for making a cyclohexylbenzene hydroperoxide product, the process comprising:

(I) providing a first liquid mixture comprising cyclohexylbenzene and cyclohexylbenzene hydroperoxide;

(II) forming a second vapor/liquid mixture stream and a second liquid stream by passing the first liquid mixture through a first thin-film evaporation device under a first absolute pressure of at most 80 kPa;

(III) separating the second vapor/liquid mixture stream in a first separation zone under a second absolute pressure of at most 80 kPa to obtain a third liquid stream and a third vapor stream;

(IV) condensing a part of the third vapor stream to obtain a fourth liquid stream and a fourth vapor stream;

(V) recycling at least a part of the fourth liquid stream to the first separation zone; and (VI) obtaining the cyclohexylbenzene hydroperoxide product having a higher concentration of cyclohexylbenzene hydroperoxide compared to the first liquid mixture from the second liquid stream and/or the third liquid stream.

The cyclohexylbenzene hydroperoxide contained in the first liquid mixture can be a pure isomer having any of the formulas (F-I), (F-II), (F-III), and (F-IV) above, or a mixture comprising at least two thereof at any proportion. In the process for making phenol and cyclohexanone from cyclohexylbenzene hydroperoxide, it is highly desirable that the cyclohexylbenzene hydroperoxide in the first liquid mixture comprises phenyl-1-cyclohexyl-1-hydroperoxide at a concentration of at least A1 wt %, where A1 can be, e.g., 80, 85, 88, 90, 92, 94, 95, 96, 97, 98, or even 99, to obtain a high yield of phenol and cyclohexanone, where the percentage is based on the total weight of all isomers of cyclohexylbenzene hydroperoxide.

Based on the total weight of the first liquid mixture, the first liquid mixture may comprise from x1 wt % to x2 wt % of cyclohexylbenzene hydroperoxide, and y1 wt % to y2 wt % of cyclohexylbenzene, where x1 can be, e.g., 2, 4, 5, 8, 10, 15, 20, 25, 28, and 30; x2 can be, e.g., 60, 55, 50, 45, 40, 35, 30, 25, 20, 15, as long as x1<x2; y1 can be, e.g., 40, 45, 50, 55, 60, 65, 70, 75, 80, 85, and 90; and y2 can be, e.g., 95, 90, 85, 80, 75, 70, 65, 60, 55, and 50, as long as y1<y2. In addition to cyclohexylbenzene hydroperoxide and cyclohexylbenzene, the first liquid mixture may comprise other materials, such as solvent, water, catalyst, and the like. Desirably, the first liquid mixture comprises z1 wt % to z2 wt % of cyclohexylbenzene and cyclohexylbenzene hydroperoxide in total, based on the total weight of the first liquid mixture, where z1 can be, e.g., 80, 85, 90, 95, and 98; and z2 can be, e.g., 85, 90, 95, 98, 99, or even 100.

After the first liquid mixture has been treated in the first evaporation device and the first separation zone, cyclohexylbenzene is preferentially removed from the first liquid mixture compared to cyclohexylbenzene hydroperoxide because the vapor pressure of cyclohexylbenzene is significantly higher than cyclohexylbenzene hydroperoxide at a given operation temperature, resulting in a higher concentration of cyclohexylbenzene hydroperoxide in the second liquid stream or the third liquid stream. Thus, compared to the first liquid mixture, the cyclohexylbenzene hydroperoxide concentration in the second liquid mixture and/or the third liquid mixture may be at least A2 wt % higher, where A2 can be, e.g., 5, 8, 10, 12, 15, 18, 20, 22, 25, 28, 30, 32, 35, 38, 40, 42, 45, 48, 50, 52, 55, 58, or even 60. As such, depending on the composition of the first liquid mixture, the second liquid mixture may comprise, e.g., a1 wt % to a2 wt % of cyclohexylbenzene hydroperoxide based on the total weight of the second liquid mixture, where a1 can be, e.g., 30, 32, 35, 38, 40, 45, 50, 55, and a2 can be, e.g., 60, 58, 55, 52, 50, 45, 40, 35, as long as a1<a2. Depending on the composition of the first liquid mixture, the third liquid mixture may comprise, e.g., a3 wt % to a4 wt % of cyclohexylbenzene hydroperoxide based on the total weight of the second liquid mixture, where a3 can be, e.g., 30, 32, 35, 38, 40, 45, 50, 55, and a4 can be, e.g., 60, 58, 55, 52, 50, 45, 40, 35, as long as a3<a4.

The final cyclohexylbenzene hydroperoxide product is derived from the second liquid mixture, the third liquid mixture or a combination of the second liquid mixture and the third liquid mixture. Preferably, the second liquid mixture is used directly as the final cyclohexylbenzene hydroperoxide product. Alternatively, a mixture of the second liquid mixture and the third liquid mixture can be used directly as the final cyclohexylbenzene hydroperoxide product. Alternatively, the second liquid mixture, or the third liquid mixture, or a combination of the second liquid mixture and the third liquid mixture can be subjected to further treatment, including but not limited to additional concentration, to obtain the final cyclohexylbenzene hydroperoxide product.

Thus, the final cyclohexylbenzene hydroperoxide product obtained according to the present disclosure may comprise, e.g., from b1 wt % to b2 wt % of cyclohexylbenzene hydroperoxide based on the total weight of the final cyclohexylbenzene hydroperoxide product, where b1 can be, e.g., 30, 35, 40, 45, 50, 55, 60, 65, 70, 75, and b2 can be, e.g., 90, 85, 80, 75, 70, 65, 60, 55, 50, 45, 50, as long as b1<b2.

Cyclohexylbenzene hydroperoxide undergoes thermal decomposition at certain temperatures, e.g., at above 150° C. Other organic hydroperoxides, such as cumene hydroperoxide, undergo thermal degradation at elevated temperature as well. Thus, it is highly desired that the removal of a hydrocarbon such as cyclohexylbenzene from a hydrocarbon-hydroperoxide mixture should be conducted at temperature below the thermal degradation temperature of the organic hydroperoxide. The hydrocarbon to be removed may have a high boiling temperature resulting in a low partial pressure thereof at a temperature below the thermal degradation temperature of the organic hydroperoxide. For example, cyclohexylbenzene has a relatively high boiling temperature under normal conditions (about 240° C.) which is well above the thermal degradation temperature of cyclohexylbenzene hydroperoxide. In such cases, it is highly desired that the removal of the high-boiling point hydrocarbon from the mixture by distillation should be conducted at a reduced pressure. In addition, to obtain significant amount of vapor of the high-boiling point hydrocarbon at a relatively low temperature in a short period of time, it is highly desired that the liquid phase of the hydrocarbon-hydroperoxide mixture has a large surface area. To that end, a thin-film evaporation device is used as the first evaporation device in the present disclosure.

Thin-film evaporation devices operate by forming a thin film of the treated liquid material, which partly vaporizes to produce a vapor phase and/or a vapor/liquid mixture. The thin film can be formed over a solid surface by mechanical distribution means or gravity. A particularly desirable evaporation device for the present disclosure is a falling film evaporator, in which the first liquid mixture travels downward on a solid surface as a falling film. An example of the falling film evaporator is a heat exchanger comprising multiple tubes, where the first liquid mixture is distributed either on the shell side or the tube side and flows downwardly on the external or internal walls of the tubes, and the heating media (such as steam) travels on the opposite side providing the thermal energy required for vaporizing part of the liquid material in the falling film. As a result of partial evaporation, a second liquid stream comprising cyclohexylbenzene hydroperoxide at a higher concentration than the first liquid mixture and a second vapor/liquid mixture stream comprising higher concentration of cyclohexylbenzene than the first liquid stream are produced. The liquid stream may exit the first evaporation device at the lower end and the second vapor/liquid mixture stream exits at the opposite, upper end. Alternatively, both the second liquid stream and the second vapor/liquid mixture stream exit the first evaporation device at the lower end of the device, where the flow of the second liquid stream is largely driven by gravity, and the flow of the second vapor/liquid stream is driven by a pressure differential, e.g., vacuum drawn from the lower end of the first evaporation device.

The first evaporation device may comprise multiple thin-film evaporation units, such as falling film evaporators working in parallel and/or in series. The first evaporation device may comprise at least X falling film evaporators operating in parallel with each other, where X can be, e.g., 2, 3, 4, 5, 6, 7, 8, 9, 10, 15, 20, 25, 30, 35, 40, 45, 50, or even a larger number. Small-capacity falling film evaporators can be more easily controlled in terms of working parameters including pressure drop and temperature uniformity, than large-scale units. The use of multiple small units operating in parallel enables large aggregate processing capacity for the first evaporation device if desired.

It is highly desired that the first liquid mixture is heated to a temperature lower than the thermal degradation temperature of cyclohexylbenzene hydroperoxide in the first evaporation device. To that end, it is desired that the temperature of the heating media, such as stream, is at least Y° C. lower than the thermal degradation temperature of cyclohexylbenzene hydroperoxide, where Y can be, e.g., 10, 15, 20, 25, 30, 35, 40, 45, or 50. Preferably, the temperature of the first liquid mixture in the first evaporation device is controlled at no greater than Z1° C., where Z1 can be, e.g., 110, 105, 100, 95, 90, 80, or even 75. Nonetheless, to enable a relatively high rate of evaporation of the first liquid mixture, the temperature of the first liquid mixture in the first evaporation device may be desirably higher than Z2° C., where Z2 can be, e.g., 80, 85, 90, 95, or 100.

To effectively evaporate the first liquid mixture, a vacuum is applied to the first evaporation device. Thus, the internal absolute pressure inside the first evaporation device is in a range from P1 kPa to P2 kPa, where P1 can be, e.g., 0.1, 0.2, 0.3, 0.4, 0.5, 0.6, 0.7, 0.8, 0.9, 1.0, 1.2, 1.4, 1.5, 1.6, 1.8, 2.0, 2.5, 3.0, 3.5, 4.0, 4.5, 5.0, 6.0, 7.0, 8.0, 9.0, 10, 20; and P2 can be, e.g., 80, 70, 60, 50, 40, 30, 20, 10, 8.0, 6.0, 5.0, 4.0, 3.0, 2.0, 1.0, as long as P1<P2.

The first separation zone can be located immediately below the first evaporation device. For example, the first separation zone and the first evaporation device can form an integral structure, such that in the upper part of the structure, the evaporation occurs to create a second liquid stream and a second vapor/liquid stream, and in the lower part of the structure, the vapor/liquid phase created in the upper part are separated to form the third liquid stream and the third vapor stream. The third liquid stream may advantageously combine with the second liquid stream.

Preferably, especially where the first evaporation device comprises multiple evaporators such as falling film evaporators, the first evaporation device and the first separation zone may be substantially discrete components in fluid communication with each other. The second liquid stream may exit the first evaporation device without passing through the first separation zone, and only the second vapor/liquid mixture stream passes through the first separation zone, where the third liquid stream and the third vapor stream are created. Desirably, the third liquid stream travels downwards due to gravity, and the third vapor stream travels upwards due to pressure differential, such as a vacuum applied to the first separation zone. Preferably, the first evaporation device may comprise multiple falling film evaporators producing multiple streams of liquid which are combined to form the second liquid stream, and multiple streams of vapor/liquid mixture which are channeled into a central first separation zone, where the third vapor stream and the third liquid stream are produced.

Preferably, the first separation zone may comprise a separation drum having a stage inside contacting the second vapor/liquid stream. The stage may include at least one of (i) a layer of packing material; (ii) a plurality of plates; and (iii) a plurality of trays. The stage may comprise, e.g., N1 to N2 theoretical trays, where N1 and N2 can be, e.g., 1, 2, 3, 4, 5, 6, 7, 8, 9, 10, 11, 12, 13, 14, 15, 16, 17, 18, 19, 20, as long as N1≤N2.

Preferably, at least a part of the second liquid stream can be recycled to the first evaporation device. The part of the second liquid stream recycled to the first evaporation device can represent a1% to a2% of the total quantity of the second liquid stream, where a1 and a2 can be, e.g., 80, 82, 84, 86, 88, 90, 92, 94, 95, 96, 97, 98, 99, as long as a1≤a2. The higher this recycle rate, the higher the concentration of cyclohexylbenzene hydroperoxide can be in the second liquid stream exiting the first evaporation device.

Preferably, at least a part of the third liquid stream may be recycled to the first evaporation device. The part of the third liquid stream recycled to the first evaporation device can represent b1% to b2% of the total quantity of the third liquid stream, where b1 and b2 can be, e.g., 80, 82, 84, 86, 88, 90, 92, 94, 95, 96, 97, 98, 99, as long as b1≤b2. The higher this recycle rate, the higher the concentration of cyclohexylbenzene hydroperoxide can be in the third liquid stream exiting the first separation zone.

Preferably, both a part of the second liquid stream and a part of the third liquid stream may be recycled to the first evaporation device. The part of the second and third liquid streams recycled to the first evaporation device can represent c1% to c2% of the total quantity of the second and third liquid streams, where c1 and c2 can be, e.g., 80, 82, 84, 86, 88, 90, 92, 94, 95, 96, 97, 98, 99, as long as c1≤c2. The higher this recycle rate, the higher the concentration of cyclohexylbenzene hydroperoxide can be in the second and third liquid streams combined entering the next process step such as additional concentration or cleavage reaction.

The third vapor stream produced in the first separation zone comprises both cyclohexylbenzene and cyclohexylbenzene hydroperoxide. In the processes of the present disclosure, the third vapor stream is subjected to partial condensation by passing through a first condensing heat exchanger to obtain a fourth liquid stream and a fourth vapor stream. Due to the higher vapor pressure of cyclohexylbenzene than cyclohexylbenzene hydroperoxide at the condensing temperature, cyclohexylbenzene hydroperoxide in the third vapor stream is preferentially condensed. At least a part of the fourth liquid stream can be recycled to the first evaporation device. The part of the fourth liquid stream recycled to the first evaporation device can represent d1% to d2% of the total quantity of the fourth liquid stream, where d1 and d2 can be, e.g., 80, 82, 84, 86, 88, 90, 92, 94, 95, 96, 97, 98, 99, as long as d1≤d2. A part of the fourth liquid stream may be recycled to another process step, such as cyclohexylbenzene oxidation where cyclohexylbenzene is oxidized to make a part of the first liquid mixture containing cyclohexylbenzene hydroperoxide.

Preferably, the first condensing heat exchanger may be at least partly located inside the first separation zone. This configuration enables minimal pressure drop caused by the first condensing heat exchanger. Alternatively, the first condensing heat exchanger may be located outside of the first separation zone, such that the third vapor stream exits the vessel housing the first separation zone and enters the first condensing heat exchanger through a conduit. Because high vacuum is desired for effective evaporation of the first liquid mixture, and the separation of the second vapor/liquid mixture in the first separation zone, the pressure drop caused by the extra conduit connecting the first condensing heat exchanger and the first separation zone can be less than desirable.

Alternatively, the fourth vapor stream produced at the first condensing heat exchanger may be further condensed, advantageously by a second heat exchanger located outside of the first separation zone operating at a substantially lower temperature than the first condensing heat exchanger, to produce a fifth liquid stream and a fifth vapor stream. The fifth liquid stream may be partly recycled to the first evaporation device or another process step such as oxidation. The fifth vapor stream, now with a substantially smaller quantity than the fourth vapor stream and consists essentially of materials (mainly cyclohexylbenzene) having boiling points lower than cyclohexylbenzene hydroperoxide, can be directly delivered to a vacuum pump system, where it is collected and recycled to another process step if desired. It is highly desired that the vacuum source to the sub-system including the first evaporation device, the first separation zone, the first condensing exchanger, and the second condensing exchanger is connected only to the vapor outlet of the second condensing exchanger to reduce the load of the vacuum pump.

The second liquid stream, the third liquid stream or a combination thereof may be used directly as the cyclohexylbenzene hydroperoxide product in the next process step. However, if even higher concentration of cyclohexylbenzene hydroperoxide or an even lower concentration of cyclohexylbenzene is desired in the cyclohexylbenzene hydroperoxide product, one can pass at least a part of the second fluid stream and/or a part of the third liquid stream to a second evaporation device and a second separation zone to further remove cyclohexylbenzene therefrom. Thus, step (VI) may comprise the following steps:

(VI-1) passing at least a part of the second liquid stream and/or a part of the third liquid stream through a second thin-film evaporation device to form a sixth vapor/liquid mixture stream and a sixth liquid stream;

(VI-2) separating the sixth vapor/liquid mixture stream in a second separation zone under a third absolute pressure of at most 80 kPa to obtain a seventh vapor stream and a seventh liquid stream;

(VI-3) condensing at least a part of the seventh vapor stream to obtain an eighth liquid stream; and (VI-4) obtaining the cyclohexylbenzene hydroperoxide product from the seventh liquid stream and/or the sixth liquid stream.

The second thin-film evaporation device and the second separation zone may operate according to the same principle of the first thin-film evaporation device and the first separation zone under substantially similar conditions.

The second thin-film evaporation device may comprise one or more discrete evaporators such as falling film evaporators. Because the volume of material fed into the second thin-film evaporation device is significantly smaller than that of the material fed into the first thin-film evaporation device, the capacity of the second thin-film evaporation device and the second separation zone can be smaller than the first thin-film evaporation device and the first separation zone, respectively.

In the second thin-film evaporation device, the at least a part of the seventh liquid stream and/or a part of the sixth liquid stream is heated to a second evaporation temperature not higher than the thermal degradation temperature of cyclohexylbenzene hydroperoxide. To that end, it is desired that the temperature of the heating media, such as steam, is at least $Y1°$ C. lower than the thermal degradation temperature of cyclohexylbenzene hydroperoxide, where Y1 can be, e.g., 10, 15, 20, 25, 30, 35, 40, 45, or 50. Preferably, the temperature of the liquid medium in the second thin-film evaporation device may be controlled at no greater than $Z2°$ C., where Z2 can be, e.g., 110, 105, 100, 95, 90, 80, or even 75. Nonetheless, to enable a relatively high rate of evaporation, the temperature of the liquid media in the second thin-film evaporation device may be desirably higher than $Z3°$ C., where Z3 can be, e.g., 80, 85, 90, 95, or 100.

To effectively evaporate the liquid fed into the second thin-film evaporation device, a vacuum is applied to the second evaporation device. Thus, the internal absolute pressure inside the second evaporation device is in a range from P1 kPa to P2 kPa, where P1 can be, e.g., 0.1, 0.2, 0.3, 0.4, 0.5, 0.6, 0.7, 0.8, 0.9, 1.0, 1.2, 1.4, 1.5, 1.6, 1.8, 2.0, 2.5, 3.0, 3.5, 4.0, 4.5, 5.0, 6.0, 7.0, 8.0, 9.0, 10, 15, 20; and P2 can be, e.g., 80, 70, 60, 50, 40, 30, 20, 15, 10, 8.0, 6.0, 5.0, 4.0, 3.0, 2.0, 1.0, as long as P1<P2. However, because cyclohexylbenzene concentration in the feed to the second thin-film evaporation device is lower than in the first liquid mixture, lower absolute pressures inside the second thin-film evaporation device and the second separation zone than inside the first thin-film evaporation device and the second separation zone are highly desired in order to effectively remove cyclohexylbenzene from the second and/or third liquid streams fed into the second thin-film evaporation device. Thus, the third absolute pressure may be at least X kPa lower than the first absolute pressure, where X can be, e.g., 0.01, 0.02, 0.03, 0.04, 0.05, 0.06, 0.07, 0.08, 0.09, 0.10, 0.12, 0.14, 0.15, 0.16, 0.18, 0.20, 0.25, 0.30, 0.35, 0.40, 0.45, 0.50, 0.60, 0.70, 0.80, 0.90, 1.00, 1.50, 2.00, 2.50, 3.00, 3.50, 4.00, 4.50, or 5.00.

The second separation zone can be located immediately below the second evaporation device. For example, the second separation zone and the second evaporation device can form an integral structure, such that in the upper part thereof, the evaporation occurs to create a seventh liquid stream and a seventh vapor/liquid stream, and in the lower part, the vapor/liquid phase created in the upper part is separated to form the eighth liquid stream and the eighth vapor stream. The seventh liquid stream may advantageously combine with the eighth liquid stream.

Preferably, especially where the second evaporation device comprises multiple evaporators such as falling film evaporators, the second evaporation device and the second separation zone are substantially discrete components in fluid communication with each other. The seventh liquid stream may exit the second evaporation device without passing through the second separation zone, and only the seventh vapor/liquid mixture stream enters the second separation zone, where the eighth liquid stream and the eighth vapor stream are created. Desirably, the seventh liquid stream travels downwards in the second separation zone due to gravity, and the seventh vapor stream travels upwards in the second separation zone due to pressure differential, such as a vacuum. Preferably, the second thin-film evaporation device may comprise multiple falling film evaporators producing multiple streams of liquid which are combined to form the seventh liquid stream, and multiple streams of vapor/liquid mixture which are channeled into a central second separation zone, where the eighth vapor stream and the eighth liquid stream are produced. Preferably, both the seventh liquid stream and the seventh vapor/liquid mixture stream are introduced into the second separation zone, where the vapor/liquid mixture travels upwards due to a pressure differential and separated to create the eighth liquid stream and the eighth vapor stream, and the seventh and eighth liquid streams are combined and passed to the next process step as the cyclohexylbenzene hydroperoxide product.

Preferably, the second separation zone comprises a separation drum having a stage inside contacting the seventh vapor/liquid mixture stream. The stage may include at least one of (i) a layer of packing material; (ii) a plurality of plates; and (iii) a plurality of trays. The stage may comprise, e.g., N1 to N2 theoretical trays, where N1 and N2 can be, e.g., 1, 2, 3, 4, 5, 6, 7, 8, 9, 10, 11, 12, 13, 14, 15, 16, 17, 18, 19, 20, as long as N1≤N2. Alternatively, the second separation zone may comprise no stage, and the seventh vapor/liquid mixture stream may be allowed to separate at least partly while travelling upwards due to the pressure differential applied by a second vacuum system.

At least a part of the seventh liquid stream may be recycled to the second and/or the first evaporation device(s). The part of the seventh liquid stream recycled to the second and/or first evaporation device(s) can represent r1% to r2% of the total quantity of the liquid material fed into the second evaporation device, where r1 and r2 can be, e.g.: 1, 2, 3, 4, 5, 6, 7, 8, 9, 10, 15, 20, 25, 30, 35, 40, 45, 50, 55, 60, 65, 70, 75, 80, 85, 90, as long as r1≤r2. The higher this recycle rate, the higher the concentration of cyclohexylbenzene hydroperoxide can be in the seventh liquid stream exiting the first evaporation device.

At least a part of the eighth liquid stream may be recycled to the second and/or the first evaporation device(s). The part of the eighth liquid stream recycled to the second and/or first evaporation device(s) can represent s1% to s2% of the total quantity of the eighth liquid stream, where s1 and s2 can be, e.g.: 1, 2, 3, 4, 5, 6, 7, 8, 9, 10, 15, 20, 25, 30, 35, 40, 45, 50, 55, 60, 65, 70, 75, 80, 85, 90, as long as s1≤s2. The higher this recycle rate, the higher the concentration of cyclohexylbenzene hydroperoxide can be in the eighth liquid stream exiting the second separation zone.

Alternatively, both a part of the seventh liquid stream and a part of the eighth liquid stream may be recycled to the first evaporation device. The part of the seventh and eighth liquid streams recycled to the first evaporation device can represent t1% to t2% of the total quantity of the second and third liquid streams, where t1 and t2 can be, e.g.: 20, 25, 30, 35, 40, 45, 50, 55, 60, 65, 70, 75, 80, 85, 90, as long as t1≤t2. The higher this recycle rate, the higher the concentration of cyclohexylbenzene hydroperoxide can be in the seventh and eighth liquid streams combined entering the next process step such as cleavage reaction.

The eighth vapor stream produced in the second separation zone comprises both cyclohexylbenzene and cyclohexylbenzene hydroperoxide. In the processes of the present disclosure, the eighth vapor stream can be subjected to partial condensation by passing through a third condensing heat exchanger to obtain a ninth liquid stream and a ninth vapor stream. Due to the higher vapor pressure of cyclohexylbenzene than cyclohexylbenzene hydroperoxide at the condensing temperature, cyclohexylbenzene hydroperoxide in the eighth vapor stream is preferentially condensed. At least a part of the ninth liquid stream can be recycled to the first evaporation device. The part of the ninth liquid stream recycled to the first evaporation device can represent u1% to u2% of the total quantity of the ninth liquid stream, where u1 and u2 can be, e.g., 30, 40, 50, 60, 70, 80, 82, 84, 86, 88, 90, 92, 94, 95, 96, 97, 98, 99, as long as u1≤u2. The higher this recycle rate, the higher the concentration of cyclohexylbenzene can be in the ninth vapor stream exiting the third condensing heat exchanger. A part of the ninth liquid stream may be recycled to another process step, such as cyclohexylbenzene oxidation where cyclohexylbenzene is oxidized to make a part of the first liquid mixture containing cyclohexylbenzene hydroperoxide.

Preferably, the third condensing heat exchanger may be at least partly located inside the second separation zone. This configuration enables minimal pressure drop caused by the third condensing heat exchanger. Because a very low absolute pressure inside the second separation zone and the second evaporation device is highly desired, as described above, this configuration, especially where the third condensing heat exchanger is completed located within the second evaporation zone, can be particularly advantageous. Alternatively, the third condensing heat exchanger may be located outside of the first separation zone, such that the eighth vapor stream exits the vessel housing the second separation zone and enters the third condensing heat exchanger through a conduit. Because vacuum is highly desired for effective evaporation of the seventh liquid stream, and the separation of the seventh vapor/liquid mixture stream in the second separation zone, the pressure drop caused by the extra conduit connecting the third condensing heat exchanger and the second separation zone can be less than desirable.

The ninth vapor stream, now with a substantially smaller quantity than the eighth vapor stream and consists essentially of materials (mainly cyclohexylbenzene) having boiling points lower than cyclohexylbenzene hydroperoxide, can be directly delivered to a second vacuum pump system, where it is collected and recycled to another process step if desired as described above. It is highly desired that the vacuum source to the subsystem including the second thin-film evaporation device, the second separation zone and the third condensing exchanger, is connected only to the vapor outlet of the third condensing exchanger to reduce the load of the vacuum pump.

The subsystem comprising the first thin-film evaporation device, the first separation zone, the first condensing heat exchanger, and the second condensing heat exchanger can be called the first separation sub-system in the present disclosure. The subsystem including the second thin-film evaporation device, the second separation zone, and the third condensing heat exchanger can be called the second separation sub-system. The first vacuum system connected to the first separation sub-system and the second vacuum system connected to the second separation sub-system can be the same and single vacuum system or separate vacuum systems. It is highly desired that the connection delivering liquid feed material from the first separation sub-system to the second separation sub-system, if any, is sealed by a liquid material during normal operation and/or regulated by a valve, such that the pressure in the first sub-system and the second sub-system can be individually and separately controlled.

The first and/or second vacuum systems advantageously comprise a vacuum pump, a compressor or other vacuum generator. Preferably, a liquid-ring vacuum pump capable of producing the desired level of low pressure may be used. Preferably, the sealant liquid used in the liquid-ring pump may be cyclohexylbenzene. The cyclohexylbenzene liquid sealing material can be derived directly or indirectly from one or more of the fifth vapor stream, the fifth liquid stream, the eighth vapor stream, the ninth liquid stream, and the ninth liquid stream. The cyclohexylbenzene sealing liquid may be recycled to a cyclohexylbenzene oxidation step to produce a part of the first liquid mixture.

As discussed above, due to the high boiling temperature of cyclohexylbenzene, and its low vapor pressure at the operation temperature in the thin-film evaporation devices, it is highly desired that a low absolute pressure (i.e., high vacuum) is applied to the separation system(s) to effectively remove cyclohexylbenzene from the cyclohexylbenzene/ cyclohexylbenzene hydroperoxide mixture. To that end, pressure drop in the separation system from the vacuum pump to the evaporation devices should be minimized Thus, it is highly desired that the vessels and conduits are designed such that the vapor phase(s) and vapor/liquid mixture streams travel at a nominal velocity lower than sonic velocity, e.g., lower than V1 m·s-1, where V1 can be 320, 300, 280, 260, 250, 240, 220, 200, 180, 160, 150, 140, 120, 100, 80, 70, 60, 50, 40, 30, 20; or lower than f·Vs, where Vs is sonic velocity under the given temperature and pressure, and f is a factor such as 0.8, 0.7, 0.6, 0.5, 0.4, 0.3, 0.2, or even 0.1. This can be achieved, in part, by placing the first and third condensing heat exchangers inside the vessel of the first separation zone and the second separation zone.

To minimize the thermal degradation of cyclohexylbenzene hydroperoxide in the cyclohexylbenzene hydroperoxide product, it is highly desired that the residence time of the cyclohexylbenzene hydroperoxide product at high temperature is minimized To that end, preferably, the cyclohexylbenzene hydroperoxide product, be it drawn from the second liquid stream, the third liquid stream, a combination of the second and third liquid streams, the seventh liquid stream, the eighth liquid stream, or a combination of the seventh and eighth liquid streams, may be quenched immediately after exiting the separation system to a lower temperature, such as a temperature at least 50° C., 45° C., 40° C., 30° C., 25° C., 20° C., 18° C., 15° C., 14° C., 10° C., or 5° C. lower than immediately exiting the separation system, or a temperature at least 20° C., 25° C., 30° C., 35° C., 45° C., or 50° C., lower than the thermal degradation temperature of cyclohexylbenzene hydroperoxide. Specifically, the cyclohexylbenzene hydroperoxide product may be quenched to a temperature no greater than 100° C., 95° C., 90° C., 85° C., 80° C., 75° C., 70° C., 65° C., or 60° C., immediately upon exiting the separation system. Preferably, the cyclohexylbenzene hydroperoxide product may be quenched to 80° C. in a period of no greater than T minutes immediately upon exiting the separation system, where T can be, e.g., 20, 18, 16, 15, 14, 12, 10, 8, 6, 5, 4, 3, 2, 1, or 0.5.

As mentioned above and to be described in greater detail below, the cyclohexylbenzene hydroperoxide in the first liquid mixture may be produced by an aerobic oxidation of cyclohexylbenzene in the presence of a catalyst. In such case, the cyclohexylbenzene-containing streams such as the third liquid stream, the fourth liquid stream, the fifth liquid stream, the sixth liquid stream, the sixth vapor stream, the ninth liquid stream, and the ninth vapor stream may be recycled to the oxidation step to produce a part of the first liquid mixture to be treated by the process of the present disclosure.

One use of the cyclohexylbenzene hydroperoxide product made according to the present disclosure is for making phenol and cyclohexanone by subjecting the cyclohexylbenzene hydroperoxide in the product to a cleavage reaction in the presence of an acid catalyst. The catalyst can be a liquid, such as sulfuric acid, phosphorous acid, hyperchloric acid, and the like, or a solid acid, such as faujasite. The cyclohexylbenzene hydroperoxide product made according to the present disclosure may be diluted before being fed into a cleavage reactor. In any event, due to the reduced cyclohexylbenzene concentration in the cyclohexylbenzene hydroperoxide product, undesirable side reactions in the cleavage reactor is reduced, and the yield of phenol and cyclohexanone is enhanced.

In a second aspect of the present disclosure, a method for making an organic hydroperoxide product from a mixture containing a hydrocarbon and its corresponding hydroperoxide is provided. The method can be used to make organic hydroperoxides such as cumene hydroperoxide, cyclohexylbenzene hydroperoxide, sec-butylbenzene hydroperoxide, and the like. The above description of the method for making cyclohexylbenzene hydroperoxide according to the first aspect of the present disclosure can be adapted for making organic hydroperoxides other than cyclohexylbenzene hydroperoxide.

The Integrated Process for Making Phenol and/or Cyclohexanone from Benzene

The process of the present disclosure has particular application as part of an integrated process for the conversion of benzene to phenol and chonone, which is described summarily below.

In such an integrated process the benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to biphenyl followed by hydrogenation of the biphenyl. However, in practice, the cyclohexylbenzene can be produced by contacting the benzene with hydrogen under hydroalkylation conditions in the presence of a hydroalkylation catalyst whereby the benzene undergoes the following reaction (1) to produce cyclohexylbenzene (CHB):

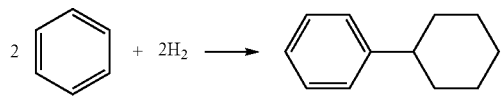

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from 100° C. to 400° C., such as from 125° C. to 250° C., while suitable reaction pressures are from 100 kPa to 7,000 kPa, such as from 500 kPa to 5,000 kPa. Suitable values for the molar ratio of hydrogen to benzene are from 0.15:1 to 15:1, such as from 0.4:1 to 4:1, for example, from 0.4:1 and 0.9:1.

The catalyst employed in the hydroalkylation reaction is generally a bifunctional catalyst comprising a molecular sieve of the MCM-22 type and a hydrogenation metal.

Any known hydrogenation metal can be employed in the hydroalkylation catalyst, although suitable metals include palladium, ruthenium, nickel, zinc, tin, and cobalt, with palladium being particularly advantageous. For example, the amount of hydrogenation metal present in the catalyst may be from 0.05 wt % to 10 wt %, such as from 0.1 wt % to 5.0 wt %, of the catalyst. Where the MCM-22 type molecular sieve is an aluminosilicate, the amount of hydrogenation metal present may be such that the molar ratio of the aluminum in the molecular sieve to the hydrogenation metal is from 1.5 to 1500, for example, from 75 to 750, such as from 100 to 300.

The hydrogenation metal may be directly supported on the MCM-22 type molecular sieve by, for example, impregnation or ion exchange. However, preferably, at least 50 wt %, for example at least 75 wt %, and even substantially all of the hydrogenation metal may be supported on an inorganic oxide separate from, but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia.

The hydrogenation metal is deposited on the inorganic oxide, such as by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally 350 kPa to 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

The catalyst may comprise a binder. Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins, commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation step is highly selective towards cyclohexylbenzene, the effluent from the hydroalkylation reaction will normally contain unreacted benzene feed, some dialkylated products, and other by-products, particularly cyclohexane, and methylcyclopentane. In fact, typical selectivities to cyclohexane and methylcyclopentane in the hydroalkylation reaction are 1-25 wt % and 0.1-2.0 wt %, respectively.

A dehydrogenation reaction may be performed on all or a portion of the output of the hydroalkylation step.

Alternatively, the hydroalkylation reaction effluent may be separated into at least a (i) C6-rich composition and (ii) the remainder of the hydroalkylation reaction effluent. When a composition is described as being "rich" in a specified species (e.g., C6-rich, benzene-rich or hydrogen-rich), it is meant that the wt % of the specified species in that composition is enriched relative to the feed composition (i.e., the input). A "C6" species generally means any species containing 6 carbon atoms.

Given the similar boiling points of benzene, cyclohexane, and methylcyclopentane, it is difficult to separate these materials by distillation. Thus, a C6-rich composition comprising benzene, cyclohexane, and methylcyclopentane may be separated by distillation from the hydroalkylation reaction effluent. This C6-rich composition may then be subjected to the dehydrogenation process described above such that at least a portion of the cyclohexane in the composition is converted to benzene and at least a portion of the methylcyclopentane is converted to linear and/or branched paraffins, such as 2-methylpentane, 3-methylpentane, n-hexane, and other hydrocarbon components such as isohexane, C5 aliphatics, and C1 to C4 aliphatics. The dehydrogenation product composition may then be fed to a further separation system, typically a further distillation tower, to divide the dehydrogenation product composition into a benzene-rich stream and a benzene-depleted stream. The benzene-rich stream can then be recycled to the hydroalkylation step, while the benzene-depleted stream can be used as a fuel for the process. When a composition is described as being "depleted" in a specified species (e.g., benzene-depleted), it is meant that the wt % of the specified species in that composition is depleted relative to the feed composition (i.e., the input).

After separation of the C6-rich composition, the remainder of hydroalkylation reaction effluent may be fed to a second distillation tower to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene may be effected in a transalkylation reactor, separate from the hydroalkylation reactor, over a suitable transalkylation catalyst, including large pore molecular sieves such as a molecular sieve of the MCM-22 type, zeolite beta, MCM-68 (see U.S. Pat. No. 6,014,018), zeolite Y, zeolite USY, and mordenite. A large pore molecular sieve has an average pore size in excess of 7 Å, such as in a range from 7 Å to 12 Å. The transalkylation reaction is typically conducted under at least partial liquid phase conditions, which suitably include a temperature of 100° C. to 300° C., a pressure of 800 kPa to 3500 kPa, a weight hourly space velocity of 1 hr-1 to 10 hr-1 on total feed, and a benzene/dicyclohexylbenzene weight ratio of 1:1 to 5:1. The transalkylation reaction effluent can then be returned to the second distillation tower to recover the additional monocyclohexylbenzene product produced in the transalkylation reaction.

After separation in the second distillation tower, the cyclohexylbenzene is converted into phenol by a process similar to the Hock process. In this process, the cyclohexylbenzene is initially oxidized to the corresponding hydroperoxide. This is accomplished by introducing an oxygen-containing gas, such as air, into a liquid phase containing the cyclohexylbenzene. Unlike the Hock process, atmospheric air oxidation of cyclohexylbenzene, in the absence of a catalyst, is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo [2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzene benzenedisulphonimide. Preferably, the catalyst is N-hydroxyphthalimide. Another suitable catalyst is N,N', N"-trihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount from 0.0001 wt % to 15 wt %, such as from 0.001 wt % to 5.0 wt %, of the cyclohexylbenzene.

Suitable conditions for the oxidation step include a temperature from 70° C. to 200° C., such as 90° C. to 130° C., and an absolute pressure of 50 kPa to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

The oxidation product directly obtained from the oxidation reactor can contain, e.g., 3 wt % to 50 wt % of cyclohexylbenzene hydroperoxide, and from 50 wt % to 97 wt % of cyclohexylbenzene. While it is possible to feed this mixture of cyclohexylbenzene and cyclohexylbenzene hydroperoxide into the next process step such as cleavage, for reasons already explained above, it is highly desirable that the oxidation product is further concentrated with respect to cyclohexylbenzene hydroperoxide. The process in accordance with the present disclosure may be advantageously used to remove a part of the cyclohexylbenzene therefrom to obtain a cyclohexylbenzene hydroperoxide product with a higher cyclohexylbenzene hydroperoxide concentration.

Another reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of 20° C. to 150° C., such as 40° C. to 120° C., a pressure of 50 kPa to 2,500 kPa, such as 100 kPa to 1000 kPa. The cyclohexylbenzene hydroperoxide is preferably diluted in an organic solvent inert to the cleavage reaction, such as methyl ethyl ketone, cyclohexanone, and/or phenol, to assist in heat removal.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid, and p-toluenesulfonic acid. Ferric chloride, boron trifluoride, sulfur dioxide, and sulfur trioxide are also effective homogeneous cleavage catalysts. The preferred homogeneous cleavage catalyst is sulfuric acid, with preferred concentrations in the range of 0.05 wt % to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a clay, such as an acidic montmorillonite silica-alumina clay, as described in U.S. Pat. No. 4,870,217, the entire disclosure of which is incorporated herein by reference.

The effluent from the cleavage reaction comprises phenol and cyclohexanone in substantially equimolar amounts and, depending on demand, the cyclohexanone can be sold or can be dehydrogenated into additional phenol. Any suitable dehydrogenation catalyst can be used in this reaction, such as the dehydrogenation catalyst or a variation of the catalyst described herein. Suitable conditions for the dehydrogenation step comprise a temperature of 250° C. to 500° C. and a pressure of 0.01 atm to 20 atm (1 kPa to 2030 kPa), such as a temperature of 300° C. to 450° C. and a pressure of 1 atm to 3 atm (100 kPa to 300 kPa).

The invention will now be more particularly described with reference to the accompanying drawing.

DESCRIPTION ACCORDING TO THE DRAWING

Referring to FIG. 1, which is a schematic diagram of a process 101 according to the first aspect of the present disclosure for making a cyclohexylbenzene hydroperoxide product starting from a cyclohexylbenzene oxidation step.

In oxidation reactor 103, cyclohexylbenzene (from fresh cyclohexylbenzene stream 102 and recycle streams discussed below) is oxidized to produce a liquid oxidation product stream 105 comprising cyclohexylbenzene and cyclohexylbenzene hydroperoxide. Stream 105 is combined with liquid recycle streams 157 and 139, described in detail below, and then divided into streams 107 and 109, which are combined with recycle streams 111 and 113, respectively, and fed into falling film evaporators 119 and 121, respectively, as the first liquid mixture streams 115 and 117. By operation of liquid distributors, the first liquid mixture is distributed into a plurality of parallel, vertical tubes 123 and 125 inside the evaporators, forming downward-flowing liquid film on the internal walls thereof. Steam passing through the shell side of the evaporators heats the thin liquid film to a temperature no greater than 110° C. The first absolute internal pressure inside the evaporators 119 and 121 is about 1.3 kPa (10 torr) by operation of a vacuum pump 179 described in detail below. As a result of the heating and the low pressure, second liquid streams 131 and 133 are produced, along with second vapor/liquid mixture streams 127 and 129, which are fed into a centralized first separation zone 135.

Inside the first separation zone 135, the vapor/liquid mixture fed into the lower section thereof travels upwards due to a pressure differential produced by the vacuum pump 179, and comes into contact with a stage 137 comprising 2-10 theoretical stages. As a result, a liquid stream is formed, part of which exits the bottom of the separation zone as stream 141, and other parts of which are recycled to falling film evaporators 119 and 121 as recycle streams 111 and 113, as mentioned above. The third vapor stream 142 exiting the stage 137 travels upwards and contacts the serpentine tubes 143 containing cooling water of the first condensing heat exchanger, where it is partly condensed to form a fourth liquid stream 139 comprising cyclohexylbenzene at a concentration substantially higher than in stream 105. Stream 139 is recycled to the falling film evaporators 119 and 121 along with other recycle streams 111, 113 and 157 as described above and below. A liquid collector 145 below the first condensing heat exchanger prevents the fourth liquid stream 139 from flowing downward to the stage 137.

The fourth vapor stream 147 exiting the first separation zone 135 then passes through a second condensing heat exchanger 149 and contacts the serpentine tubes containing circulating cooling water. At the lower part of the heat exchanger, a fifth liquid stream 151 consisting essentially of cyclohexylbenzene is formed and recycled to the oxidation reactor as recycle stream. The fifth vapor stream 153 is then delivered to a liquid-ring vacuum pump 179 which uses cyclohexylbenzene as the sealant liquid. Part of the cyclohexylbenzene sealant liquid in pump 179 may be recycled to the oxidation reactor as stream 181. As shown, the vacuum in the first separation sub-system comprising the falling film evaporators 119 and 121, the first condensing heat exchanger 143, and the second condensing heat exchanger 149 is created through the connection between the vacuum pump 179 and the second condensing heat exchanger 149. Thus, the internal pressure inside the second condensing heat exchanger normally is lower than the internal pressure inside the first separation zone due to some pressure drop, which, in turn, is lower than the internal absolute pressure inside the falling film evaporators 119 and 121. It is highly desired that the pressure drop in these vessels are minimized for reasons described above. The configuration illustrated in FIG. 1 includes a first condensing heat exchanger 143 housed inside the vessel of the first separation zone, which is believed to reduce pressure drop.

In the process shown in FIG. 1, the liquid streams 131 and 133 from the falling film evaporators 119 and 121, together with the liquid stream 141 from the first separation zone 135 are combined to form a liquid stream 155, which has a significantly higher cyclohexylbenzene hydroperoxide concentration than stream 105. The system is designed such that these liquid streams form a liquid seal, effectively preventing leakage and vacuum loss through the conduits for these liquid streams. The liquid stream 155 is divided into two streams 157 and 159. Stream 157 is recycled to falling film evaporators 119 and 121. Stream 159 is delivered to a second-stage separation sub-system including a second falling film evaporator 161 and a second separation zone 167. Inside the second falling film evaporator 161, the liquid material flows downwards on the internal walls of a number of tubes 164 heated by steam flowing on the shell side, partly evaporates to form a seventh vapor/liquid mixture stream 163 and a seventh liquid stream 165. Stream 163 enters into the second separation zone 167 where an eighth liquid stream 169 and an eighth vapor stream are produced. The eighth vapor stream travels upwards and contacts the serpentine tube containing cooling water of a third condensing heat exchanger 171, producing a ninth liquid stream 175 and a ninth vapor stream 177. Stream 175, which consists essentially of cyclohexylbenzene and is prevented from flowing downwards in the second separation zone by a liquid collector 173, is recycled to the oxidation reactor 103. Vapor stream 177, consisting essentially of cyclohexylbenzene, is delivered to the vacuum pump 179.

In the process illustrated in FIG. 1, the first separation sub-system and the second separation sub-system are both connected to the same vacuum pump 179, although two separate vacuum pumps can be used as well. Pressure regulators may be used to adjust the internal pressure inside the two sub-systems to the same or different level(s). In general, the internal pressure in the second separation sub-system, particularly inside the second separation zone and the second thin-film evaporator, is controlled at a level lower than in the first sub-system. For example, it is desirable to control the internal pressure inside the second separation zone at no higher than 0.27 kPa (2 torr).

The liquid streams 165 and 169 are combined and immediately quenched by a heat exchanger 183 before being delivered to a cleavage reactor 185, to minimize thermal decomposition of cyclohexylbenzene hydroperoxide in the conduit connecting the second separation sub-system and the cleavage reactor. The temperature of the combined streams 165 and 169 may be at most 70° C. when reading the cleavage reactor.

While the present invention has been described and illustrated by reference to particular embodiments, those of ordinary skill in the art will appreciate that the invention lends itself to variations not necessarily illustrated herein. For this reason then, reference should be made solely to the appended claims for purposes of determining the true scope of the present invention.

Contents of all references cited herein are incorporated by reference in their entity.

Non-limiting embodiments and aspects of the processes and apparatuses of the present disclosure include:

E1. A process for making a cyclohexylbenzene hydroperoxide product, the process comprising:

(I) providing a first liquid mixture comprising cyclohexylbenzene and cyclohexylbenzene hydroperoxide;

(II) forming a second vapor/liquid mixture stream and/or a second liquid stream by passing the first liquid mixture through a first thin-film evaporation device under a first absolute pressure of at most 80 kPa;

(III) separating the second vapor/liquid mixture stream in a first separation zone under a second absolute pressure of at most 80 kPa to obtain a third liquid stream and a third vapor stream;

(IV) condensing a part of the third vapor stream to obtain a fourth liquid stream and a fourth vapor stream;

(V) recycling at least a part of the fourth liquid stream to the first separation zone; and (VI) obtaining the cyclohexylbenzene hydroperoxide product having a higher concentration of cyclohexylbenzene hydroperoxide compared to the first liquid mixture from the third liquid stream and/or the second liquid stream.

E2. The process of E1, wherein the cyclohexylbenzene hydroperoxide in the first liquid mixture comprises at least 80 wt % of cyclohexyl-1-phenyl-1-hydroperoxide, the percentage based on the total weight of the cyclohexylbenzene hydroperoxide in the first liquid mixture.

E3. The process of E1 or E2, wherein the first liquid mixture comprises at most 25 wt % of cyclohexylbenzene hydroperoxide, the percentage based on the total weight of the first liquid mixture.

E4. The process of E1 to E3, wherein the first liquid mixture comprises at most 40 wt % of cyclohexylbenzene hydroperoxide, and from 25 wt % to 90 wt % of cyclohexylbenzene, the percentages based on the total weight of the first liquid mixture.

E5. The process of E1 to E4, wherein the third liquid stream and/or the second liquid stream comprise from 30 wt % to 60 wt % of cyclohexylbenzene hydroperoxide, and from 30 wt % to 70 wt % of cyclohexylbenzene, the percentages based on the total weight of the third liquid stream or the second liquid stream, respectively.

E6. The process of E1 to E5, wherein the cyclohexylbenzene hydroperoxide product comprises from 40 wt % to 85 wt % of cyclohexylbenzene hydroperoxide, the percentages based on the total weight of the cyclohexylbenzene hydroperoxide product.

E7. The process of E6, wherein the cyclohexylbenzene hydroperoxide product comprises from 40 wt % to 85 wt % of cyclohexylbenzene hydroperoxide, and 5 wt % to 60 wt % of cyclohexylbenzene, the percentages based on the total weight of the cyclohexylbenzene hydroperoxide product.

E8. The process of E1 to E7, wherein the first thin-film evaporation device comprises at least one falling film evaporator.

E9. The process of E1 to E8, wherein the first thin-film evaporation device comprises at least two falling film evaporators operating in parallel with each other.

E10. The process of E1 to E9, wherein in the first thin-film evaporation device, the first liquid mixture is heated to a first evaporation temperature not higher than the thermal degradation temperature of cyclohexylbenzene hydroperoxide.

E11. The process of E1 to E10, wherein in the first thin-film evaporation device, the first liquid mixture is heated to a temperature not higher than 110° C. (e.g., not higher than 105° C., not higher than 100° C., not higher than 95° C., or not higher than 90° C.).

E12. The process of E1 to E11, wherein the first absolute pressure in the first evaporation device is at most 50 kPa (e.g., at most 30 kPa, at most 15 kPa, at most 14, 12, 9, 8, 7, 6, 5, 4, 3, 2, 1, 0.8, 0.5, 0.4, 0.2, 0.1 kPa).

E13. The process of E1 to E12, wherein the first absolute pressure is at most 10 kPa higher than the second absolute pressure.

E14. The process of E1 to E13, wherein the first separation zone is located immediately below the first thin-film evaporation device.

E15. The process of E14, wherein the first thin-film evaporation device comprises at least two falling film evaporators, and the first separation zone exists immediately below each falling film evaporator.

E16. The process of E1 to E15, wherein the first separation zone comprises a separation drum comprising a stage contacting the third vapor stream.

E17. The process of E16, wherein the stage comprises at least one of: (i) a layer of packing material, (ii) a plurality of plates, and (iii) a plurality of trays.

E18. The process of E16 or E17, wherein the stage comprises 1-20 theoretical trays.

E19. The process of E18, wherein the stage comprises 2-10 theoretical trays.

E20. The process of E1 to E19, wherein the condensing step (IV) is conducted at least partly inside the first separation zone.

E21. The process of E16, wherein the condensing step (IV) is conducted at least partly inside the first separation zone above the stage.

E22. The process of E1 to E21, wherein the condensing step (IV) is conducted at least partly outside the first separation zone.

E23. The process of E1 to E22, wherein the condensing step (IV) comprises:
(IV-1) condensing a part of the third vapor stream at a location inside the first separation zone to obtain a fourth liquid stream comprising cyclohexylbenzene and a fourth vapor stream comprising cyclohexylbenzene; and
(IV-2) condensing a part of the fourth vapor stream at a location outside the first separation zone to obtain a fifth liquid stream and a fifth vapor stream.

E24. The process of E23, wherein at least a part of the fifth vapor stream is delivered to a first vacuum pump system.

E25. The process of E23 or E24, further comprising:
(Va) recycling at least a part of the fifth liquid stream to the first separation zone.

E26. The process of E1 to E25, further comprising:
(Vb) recycling a part of the third liquid stream and/or a part of the second liquid stream to the first thin-film evaporation device.

E27. The process of E1 to E26, wherein step (VI) comprises:
(VI-1) passing at least a part of the third liquid stream and/or a part of the second liquid stream through a second thin-film evaporation device to form a sixth vapor/liquid mixture stream and a sixth liquid stream;
(VI-2) separating the sixth vapor/liquid mixture stream in a second separation zone under a third absolute pressure of at most 80 kPa to obtain a seventh vapor stream and a seventh liquid stream;
(VI-3) condensing at least a part of the seventh vapor stream to obtain an eighth liquid stream; and
(VI-4) obtaining the cyclohexylbenzene hydroperoxide product from the seventh liquid stream and/or the sixth liquid stream.

E28. The process of E27, wherein the third absolute pressure is at least 2.0 kPa (or 3.0, 4.0, 5.0, 6.0, 7.0, 8.0, 9.0, 10.0, 12.0, 14.0, 15.0, 16.0, 18.0, or 20 kPa) lower than the first absolute pressure.

E29. The process of E27 or E28, wherein the third absolute pressure is at most 20 kPa (15, 10, 5, 4, 3, 2, 1 kPa).

E30. The process of any of E27 to E29, wherein in the second thin-film evaporation device, the at least a part of the seventh liquid stream and/or a part of the sixth liquid stream is heated to a second evaporation temperature not higher than the thermal degradation temperature of cyclohexylbenzene hydroperoxide.

E31. The process of E30, wherein the second evaporation temperature is not higher than 110° C. (e.g., not higher than 105° C., not higher than 100° C., not higher than 95° C., not higher than 90° C.).

E32. The process of E30 or E31, wherein the second evaporation temperature is higher than 80° C. (e.g., higher than 85° C., 90° C., 95° C., 100° C., 105° C.).

E33. The process of E30 or E31, wherein in the first thin-film evaporation device, the first liquid mixture is heated to a first evaporation temperature, and the difference between the first evaporation temperature and the second evaporation temperature is no greater than 5° C.

E34. The process of E27 to E33, wherein step (VI-3) is conducted at least partly inside the second separation zone.

E35. The process of E27 to E34, wherein step (VI-3) is conducted at least partly outside of the second separation zone.

E36. The process of E27 to E35, wherein step (VI-3) comprises:
(VI-3a) condensing a part of the seventh vapor stream at a location inside the second separation zone to obtain the eighth liquid stream and an eighth vapor stream; and
(VI-3b) condensing a part of the eighth vapor stream at a location outside the second separation zone to obtain a ninth liquid stream and a ninth vapor stream.

E37. The process of E36, wherein step (VI-3) further comprises:
(VI-3c) recycling at least a part of the eighth liquid stream and/or the ninth liquid stream to the first evaporation device.

E38. The process of E36 or E37, wherein step (VI-3) further comprises:
(VI-3d) delivering at least a part of the ninth vapor stream to a second vacuum pump system.

E39. The process of E1 to E38, wherein the third vapor stream and the fourth vapor stream travel at a nominal velocity of less than 200 m·s$^{-1}$.

E40. The process of E1 to E39, wherein all vapor streams travel at a nominal velocity of less than 200 m·s$^{-1}$ in all vessels.

E41. The process of E1 to E40, further comprising:

(VII) quenching the cyclohexylbenzene hydroperoxide product to a temperature at least 20° C. lower than the thermal degradation temperature thereof.

E42. The process of E34, wherein in step (VII), the cyclohexylbenzene hydroperoxide product is quenched to a temperature no higher than 100° C. before being delivered to the next step (or no higher than 90° C., 85° C., 80° C., 75° C., 70° C., 60° C., 50° C.).

E43. The process of E42, wherein the cyclohexylbenzene hydroperoxide product is quenched from its highest temperature to 80° C. in a period of no greater than 10 minutes (or no greater than 8, 6, 5, 4, 3, 2 minutes).

E44. The process of E42, wherein the cyclohexylbenzene hydroperoxide product is quenched from its highest temperature to 60° C. in a period of no greater than 20 minutes (18, 16, 15, 14, 12, 10, 8, 6, 5, 4, 3, 2 minutes).

E45. The process of E1 to E43, wherein step (I) comprises:

(Ia) feeding a cyclohexylbenzene feed stream into an oxidation reactor;

(Ib) contacting the cyclohexylbenzene from step (Ia) with an $O_2$—containing gas in the presence of a catalyst to obtain a cyclohexylbenzene hydroperoxide—containing oxidation product; and (Ic) obtaining the first liquid mixture from the oxidation product.

E46. The process of E45, wherein a part of the third vapor stream is recycled to step (Ia) as a part of the cyclohexylbenzene feed stream.

E47. The process of E1 to E46, wherein a liquid-ring vacuum pump is in fluid communication with the first evaporation device and the first separation zone, enabling the first absolute pressure and the second absolute pressure below the atmospheric pressure.

E48. A process for making phenol and/or cyclohexanone, the process comprising:

(A) making a cyclohexylbenzene hydroperoxide product according to the process of E1 to E47 comprising cyclohexyl-1-phenyl-1-hydroperoxide; and (B) subjecting at least a portion of the cyclohexyl-1-phenyl-1-hydroperoxide to a cleavage reaction in the presence of an acid catalyst to obtain a cleavage product comprising phenol and cyclohexanone.

E49. The process of E48, wherein the acid catalyst comprises at least one of: sulfuric acid, perchloric acid, phosphorous acid.

E50. The process of E48 or E49, wherein step (A) comprises:

(A1) contacting benzene with hydrogen in the presence of a hydroalkylation catalyst under hydroalkylation conditions to produce a hydroalkylation product comprising cyclohexylbenzene;

(A2) contacting at least a part of the cyclohexylbenzene from step (A1) with an $O_2$—containing gas in the presence of a catalyst to obtain a cyclohexylbenzene hydroperoxide—containing oxidation product; and (A3) providing the first liquid mixture from the oxidation product.

E51. A process for making an organic hydroperoxide product, the process comprising:

(2I) providing a first liquid mixture comprising a hydrocarbon and a hydroperoxide corresponding to the hydrocarbon;

(2II) forming a second vapor/liquid mixture stream and/or a second liquid stream by passing the first liquid mixture through a first thin-film evaporation device under a first absolute pressure of at most 80 kPa;

(2III) separating the second vapor/liquid mixture stream in a first separation zone under a second absolute pressure of at most 80 kPa to obtain a third liquid stream and a third vapor stream;

(2IV) condensing a part of the third vapor stream at a location inside the first separation zone to obtain a fourth liquid stream and a fourth vapor stream;

(2V) recycling at least a part of the fourth liquid stream to the first separation zone;

(2VI) condensing a part of the fourth vapor stream at a location outside of the first separation zone to obtain a fifth liquid stream and a fifth vapor stream;

(2VII) obtaining the organic hydroperoxide product having a higher concentration of the hydroperoxide compared to the first liquid mixture from the third liquid stream and/or the second liquid stream.

E52. The process of E51, wherein the first liquid mixture comprises at most 25 wt % of the hydroperoxide, the percentage based on the total weight of the first liquid mixture.

E53. The process of E51 or E52, wherein the first liquid mixture comprises at most 40 wt % of the hydroperoxide, and from 25 wt % to 90 wt % of the hydrocarbon, the percentages based on the total weight of the first liquid mixture.

E54. The process of E51 to E53, wherein the third liquid stream and/or the second liquid stream comprise from 30 wt % to 60 wt % of the hydroperoxide, and from 30 wt % to 70 wt % of the hydrocarbon, the percentages based on the total weight of the third liquid stream or the second liquid stream, respectively.

E55. The process of E51 to E54, wherein the organic hydroperoxide product comprises from 40 wt % to 95 wt % of the hydroperoxide, the percentages based on the total weight of the organic hydroperoxide product.

E56. The process of E55, wherein the organic hydroperoxide product comprises from 40 wt % to 95 wt % of the hydroperoxide, and 5 wt % to 38 wt % of the hydrocarbon, the percentages based on the total weight of the organic hydroperoxide product.

E57. The process of E51 to E56, wherein the first thin-film evaporation device comprises at least one falling film evaporator.

E58. The process of E51 to E57, wherein the first thin-film evaporation device comprises at least two falling film evaporators operating in parallel with each other.

E59. The process of E51 to E58, wherein in the first thin-film evaporation device, the first liquid mixture is heated to a first evaporation temperature not higher than the thermal degradation temperature of the hydroperoxide.

E60. The process of E51 to E59, wherein in the first thin-film evaporation device, the first liquid mixture is heated to a temperature not higher than 110° C. (e.g., not higher than 105° C., not higher than 100° C., not higher than 95° C., not higher than 90° C.).

E61. The process of E51 to E60, wherein the first absolute pressure in the first evaporation device is at most 50 kPa (e.g., at most 30 kPa, at most 15 kPa, at most 14, 12, 9, 8, 7, 6, 5, 4, 3, 2, 1, 0.8, 0.5, kPa).

E62. The process of E51 to E61, wherein the first absolute pressure is at most 10 kPa higher than the second absolute pressure.

E63. The process of E51 to E62, wherein the first separation zone is located immediately below the first thin-film evaporation device.

E64. The process of E57, wherein the first thin-film evaporation device comprises at least two falling film evaporators, and the first separation zone exists immediately below each falling film evaporator.

E65. The process of E51 to E64, wherein the first separation zone comprises a separation drum comprising a stage contacting the third vapor stream.

E66. The process of E65, wherein the stage comprises at least one of: (i) a layer of packing material, (ii) a plurality of plates, and (iii) a plurality of trays.

E67. The process of E65 or E66, wherein the stage comprises 1-20 theoretical trays.

E68. The process of E67, wherein the stage comprises 2-10 theoretical trays.

E69. The process of E65 to E68, wherein the condensing step (2IV) is conducted above the stage.

E70. The process of E51 to E69, wherein at least a part of the fifth vapor stream is delivered to a first vacuum pump system.

E71. The process of E51 to E70, further comprising:
(2VIIa) recycling a part of the third liquid stream and/or a part of the second liquid stream to the first thin-film evaporation device.

E72. The process of E51 to E71, wherein step (2VIII) comprises:
(2VIII-1) passing at least a part of the third liquid stream and/or a part of the second liquid stream through a second thin-film evaporation device to form a sixth vapor/liquid mixture stream and a sixth liquid stream;
(2VIII-2) separating the sixth vapor/liquid mixture stream in a second separation zone under a third absolute pressure of at most 80 kPa to obtain a seventh vapor stream and a seventh liquid stream;
(2VIII-3) condensing at least a part of the seventh vapor stream to obtain an eighth liquid stream; and
(2VIII-4) obtaining the organic hydroperoxide product from the seventh liquid stream and/or the sixth liquid stream.

E73. The process of E72, wherein the third absolute pressure is at least 2.0 kPa (or 3.0, 4.0, 5.0, 6.0, 7.0, 8.0, 9.0, 10.0, 12.0, 14.0, 15.0, 16.0, 18.0, or 20 kPa) lower than the first absolute pressure.

E74. The process of E72 or E73, wherein the third absolute pressure is at most 20 kPa (15, 10, 5, 4, 3, 2, 1 kPa).

E75. The process of E51 to E73, wherein in the second thin-film evaporation device, the at least a part of the seventh liquid stream and/or a part of the sixth liquid stream is heated to a second evaporation temperature not higher than the thermal degradation temperature of the hydroperoxide.

E76. The process of E75, wherein the second evaporation temperature is not higher than 110° C. (e.g., not higher than 105° C., not higher than 100° C., not higher than 95° C., not higher than 90° C.).

E77. The process of E75 or E76, wherein the second evaporation temperature is higher than 80° C. (e.g., higher than 85° C., 90° C., 95° C., 100° C., 105° C.).

E78. The process of E72 to E76, wherein step (2VIII-3) is conducted at least partly inside the second separation zone.

E79. The process of E72 to E78, wherein step (2VIII-3) is conducted at least partly outside of the second separation zone.

E80. The process of E72 to E79, wherein step (2VIII-3) comprises:
(2VIII-3a) condensing a part of the seventh vapor stream at a location inside the second separation zone to obtain the eighth liquid stream and an eighth vapor stream; and
(2VIII-3b) condensing a part of the eighth vapor stream at a location outside the second separation zone to obtain a ninth liquid stream and a ninth vapor stream.

E81. The process of E80, wherein step (2VIII-3) further comprises:
(2VIII-3c) recycling at least a part of the eighth liquid stream and/or the ninth liquid stream to the first evaporation device.

E82. The process of E72 to E81, wherein step (2VIII-3) further comprises:
(2VIII-3d) delivering at least a part of the ninth vapor stream to a second vacuum pump system.

E83. The process of E51 to E82, wherein the third vapor stream and the fourth vapor stream travel at a nominal velocity of less than 200 m·s$^{-1}$.

E84. The process of E51 to E83, wherein all vapor streams travel at a nominal velocity of less than 200 m·s$^{-1}$ in all vessels.

E85. The process of E51 to E84, further comprising:
(2IX) quenching the organic hydroperoxide product to a temperature at least 20° C. lower than the thermal degradation temperature thereof.

E86. The process of E85, wherein in step (2IX), the organic hydroperoxide product is quenched to a temperature no higher than 100° C. before being delivered to the next step (no higher than 90° C., 85° C., 80° C., 75° C., 70° C., 60° C., 50° C.).

E87. The process of E86, wherein the organic hydroperoxide product is quenched from its highest temperature to 80° C. in a period of no greater than 10 minutes (8, 6, 5, 4, 3, 2 minutes).

E88. The process of E86, wherein the organic hydroperoxide product is quenched from its highest temperature to 60° C. in a period of no greater than 20 minutes (18, 16, 15, 14, 12, 10, 8, 6, 5, 4, 3, 2 minutes).

E89. The process of E51 to E87, wherein step (2I) comprises:
(2Ia) feeding a feed stream comprising the hydrocarbon into an oxidation reactor;
(2Ib) contacting the hydrocarbon from step (Ia) with an O$_2$—containing gas in the presence of a catalyst to obtain an oxidation product containing the hydroperoxide; and
(2Ic) obtaining the first liquid mixture from the oxidation product.

E90. The process of E89, wherein a part of the third vapor stream is recycled to step (Ia) as a part of the hydrocarbon feed stream.

E91. The process of E51 to E89, wherein a liquid-ring vacuum pump is in fluid communication with the first evaporation device and the first separation zone, enabling the first absolute pressure and the second absolute pressure below the atmospheric pressure.

E92. The process of E51 to E91, wherein the hydrocarbon is selected from cyclohexylbenzene, cumene, and sec-butylbenzene, and the hydroperoxide corresponding to the hydrocarbon is cyclohexylbenzene hydroperoxide, cumene peroxide, and sec-butylbenzene hydroperoxide, respectively.

E93. An apparatus for making a cyclohexylbenzene hydroperoxide product, comprising:
(A1) at least one first thin-film evaporation device capable of receiving a first liquid mixture comprising cyclohexylbenzene and cyclohexylbenzene hydroperoxide and operating under an absolute pressure of not higher than 80 kPa to generate a second vapor/liquid mixture stream and a second liquid stream;

(A2) a first separation device in fluid communication with the first thin-film evaporator capable of separating the second vapor/liquid mixture stream into a third vapor stream and a third liquid stream;

(A3) a first condenser capable of condensing a part of the third liquid stream to obtain a fourth liquid stream and a fourth vapor stream;

(A4) a fluid conduit capable of delivering a part of the fourth liquid stream to the first thin-film evaporation device; and (A5) a vacuum pump in fluid communication with the first separation device capable of generating an absolute pressure of at most 80 kPa inside the first separation device.

E94. The apparatus of E93, further comprising at least two first falling film evaporators operating in parallel with each other.

E95. The apparatus of E93 or E94, wherein the vacuum pump is capable of generating an absolute pressure of at most 5.0, 4.0, 3.0, 2.0, 1.0, 0.8, 0.6, 0.5, 0.3, 0.2, or 0.1 kPa inside the first separation device.

E96. The apparatus of E93 to E95, wherein the first condenser is at least partly located inside the first separation device.

E97. The apparatus of E96, wherein the first condenser is completed housed inside the first separation device.

E98. The apparatus of E93 to E97, wherein the first separation device is a separation drum.

E99. The apparatus of E93 to E98, further comprising at least two first falling film evaporators operating in parallel with each other, and the first separation device is a centralized separation drum receiving the second vapor/liquid mixture streams from the first falling film evaporators.

E100. The apparatus of E93 to E99, further comprising:

(A6) a second condenser in fluid communication with the first condenser capable of condensing a part of the fourth vapor stream to form a fifth vapor stream and a fifth liquid stream.

E101. The apparatus of E100, wherein the second condenser is located outside of the first separation device.

E102. The apparatus of E93 to E101, further comprising a fluid conduit capable of delivering at least a part of the second and/or the third liquid stream(s) to the first thin-film evaporation device.

E103. The apparatus of E93 to E102, further comprising:

(A7) at least one second thin-film evaporation device in fluid communication with the first thin-film evaporation device and/or the first separation device capable of operating under an absolute pressure of at most 5 kPa to generate a sixth vapor/liquid mixture stream and a sixth liquid stream; and (A8) a second separation device in fluid communication with the second thin-film evaporation device capable of separating the sixth vapor/liquid mixture stream to obtain a seventh liquid stream and a seventh vapor stream.

E104. The apparatus of E103, further comprising:

(A9) a third condenser capable of condensing a part of the seventh vapor stream to obtain an eighth liquid stream and an eighth vapor stream.

E105. The apparatus of E104, wherein the third condenser is located at least partly, advantageously completely, inside the second separation device.

E106. The apparatus of E93 to E105, further comprising:

(A10) a heat exchanger capable of quenching the second liquid stream, and/or the third liquid stream, and/or the seventh liquid stream.

E107. The apparatus of E93 to E106, further comprising:

(A0) an oxidation reactor capable of oxidizing cyclohexylbenzene to produce an oxidation effluent comprising cyclohexylbenzene hydroperoxide.

E108. The apparatus of E107, further comprising at least one of the following:

(A11) a fluid conduit capable of delivering at least a part of the fourth liquid stream to the oxidation reactor;

(A12) a fluid conduit capable of delivering at least a part of the fifth liquid stream to the oxidation reactor;

(A13) a fluid conduit capable of delivering at least a part of the eighth liquid stream to the oxidation reactor.

E109. The apparatus of E103 to E108, wherein the fluid communication between the second thin-film evaporation device and the first thin-film evaporation device and/or the first separation device is comprises a liquid seal and/or a valve such that the absolute pressures inside the first thin-film evaporation device and the second thin-film evaporation device can be separately and independently controlled.

E110. An apparatus for making phenol and/or cyclohexanone, comprising:

(B1) an apparatus of any of E93 to E109; and (B2) a cleavage reactor receiving at least a portion of the second liquid stream and/or the third liquid stream and/or the sixth liquid stream, and capable of allowing a cleavage reaction of cyclohexylbenzene hydroperoxide to obtain a cleavage effluent comprising phenol and cyclohexanone.

E111. An apparatus for making an organic hydroperoxide product, comprising:

(C1) at least one first thin-film evaporation device capable of receiving a first liquid mixture comprising a hydrocarbon and a hydroperoxide corresponding to the hydrocarbon and operating under an absolute pressure of not higher than 80 kPa to generate a second vapor/liquid mixture stream and a second liquid stream;

(C2) a first separation device in fluid communication with the first thin-film evaporator capable of separating the second vapor/liquid mixture stream into a third vapor stream and a third liquid stream;

(C3) a first condenser located inside the first separation device capable of condensing a part of the third liquid stream to obtain a fourth liquid stream and a fourth vapor stream;

(C4) a fluid conduit capable of delivering a part of the fourth liquid stream to the first thin-film evaporation device;

(C5) a second condenser located outside of the first separation device in fluid communication with the first condenser capable of condensing a part of the fourth vapor stream to obtain a fifth vapor stream and a fifth liquid stream; and (C6) a vacuum pump in fluid communication with the first separation device capable of generating an absolute pressure of at most 80 kPa inside the first separation device.

The invention claimed is:

1. A process for making a cyclohexylbenzene hydroperoxide product, the process comprising:

(I) providing a first liquid mixture comprising cyclohexylbenzene and cyclohexylbenzene hydroperoxide;

(II) forming a second vapor/liquid mixture stream and a second liquid stream by passing the first liquid mixture through a first thin-film evaporation device under a first absolute pressure of at most 80 kPa;

(III) separating the second vapor/liquid mixture stream in a first separation zone under a second absolute pressure of at most 80 kPa to obtain a third liquid stream and a third vapor stream;
(IV) condensing a part of the third vapor stream to obtain a fourth liquid stream and a fourth vapor stream;
(V) recycling at least a part of the second, third, and fourth liquid streams to the first thin-film evaporation device; and
(VI) obtaining the cyclohexylbenzene hydroperoxide product from the third liquid stream and/or the second liquid stream, wherein the cyclohexylbenzene hydroperoxide product has a higher concentration of cyclohexylbenzene hydroperoxide compared to the first liquid mixture.

2. The process of claim 1, wherein the first liquid mixture comprises at most 25 wt % of cyclohexylbenzene hydroperoxide, based on the total weight of the first liquid mixture.

3. The process of claim 1, wherein the cyclohexylbenzene hydroperoxide product comprises from 40 wt % to 85 wt % of cyclohexylbenzene hydroperoxide and 5 wt % to 60 wt % of cyclohexylbenzene, based on the total weight of the cyclohexylbenzene hydroperoxide product.

4. The process of claim 1, wherein the first thin-film evaporation device comprises at least two falling film evaporators operating in parallel with each other.

5. The process of claim 1, wherein in the first thin-film evaporation device, the first liquid mixture is heated to a temperature not higher than 110° C.

6. The process of claim 1, wherein the first absolute pressure in the first evaporation device is at most 5 kPa.

7. The process of claim 1, wherein the first separation zone comprises a separation drum comprising a stage contacting the third vapor stream.

8. The process of claim 1, wherein the condensing step (IV) is conducted at least partly inside the first separation zone.

9. The process of claim 1, wherein the condensing step (IV) comprises:
(IV-1) condensing a part of the third vapor stream at a location inside the first separation zone to obtain the fourth liquid stream comprising cyclohexylbenzene and the fourth vapor stream comprising cyclohexylbenzene; and
(IV-2) condensing a part of the fourth vapor stream at a location outside the first separation zone to obtain a fifth liquid stream and a fifth vapor stream.

10. The process of claim 9, further comprising:
(Va) recycling at least a part of the fifth liquid stream to the first separation zone.

11. The process of claim 1, wherein step (VI) comprises:
(VI-1) passing at least a part of the third liquid stream and/or a part of the second liquid stream through a second thin-film evaporation device to form a sixth vapor/liquid mixture stream and a sixth liquid stream;
(VI-2) separating the sixth vapor/liquid mixture stream in a second separation zone under a third absolute pressure of at most 5 kPa to obtain a seventh vapor stream and a seventh liquid stream;
(VI-3) condensing at least a part of the seventh vapor stream to obtain an eighth liquid stream; and
(VI-4) obtaining the cyclohexylbenzene hydroperoxide product from the seventh liquid stream and/or the sixth liquid stream.

12. The process of claim 11, wherein the third absolute pressure is at least 1.0 kPa lower than the second absolute pressure.

13. The process of claim 11, wherein the second evaporation temperature is not higher than 110° C.

14. The process of claim 11, wherein step (VI-3) is conducted at least partly inside the second separation zone.

15. The process of claim 11, wherein step (VI-3) comprises:
(VI-3a) condensing a part of the seventh vapor stream at a location inside the second separation zone to obtain the eighth liquid stream and an eighth vapor stream; and
(VI-3b) condensing a part of the eighth vapor stream at a location outside the second separation zone to obtain a ninth liquid stream and a ninth vapor stream.

16. The process of claim 15, wherein step (VI-3) further comprises:
(VI-3c) recycling at least a part of the eighth liquid stream and/or the ninth liquid stream to the first evaporation device.

17. The process of claim 1, wherein the third vapor stream and the fourth vapor stream travel at a nominal velocity of less than 200 m·s$^{-1}$.

18. The process of claim 1, further comprising:
(VII) quenching the cyclohexylbenzene hydroperoxide product to a temperature at least 20° C. lower than the thermal degradation temperature thereof.

19. The process of claim 1, wherein step (I) comprises:
(Ia) feeding a cyclohexylbenzene feed stream into an oxidation reactor;
(Ib) contacting the cyclohexylbenzene from step (Ia) with an $O_2$-containing gas in the presence of a catalyst to obtain a cyclohexylbenzene hydroperoxide-containing oxidation product; and
(Ic) obtaining the first liquid mixture from the oxidation product.

20. The process of claim 19, wherein a part of the cyclohexylbenzene in the third vapor stream is recycled to step (Ia) as a part of the cyclohexylbenzene feed stream.

21. A process for making phenol and/or cyclohexanone, the process comprising:
(A) making a cyclohexylbenzene hydroperoxide product according to the process of claim 1, where the cyclohexylbenzene hydroperoxide product comprises cyclohexyl-1-phenyl-1-hydroperoxide; and
(B) subjecting at least a portion of the cyclohexyl-1-phenyl-1-hydroperoxide to a cleavage reaction in the presence of an acid catalyst to obtain a cleavage product comprising phenol and cyclohexanone.

22. A process for making an organic hydroperoxide product, the process comprising:
(2I) providing a first liquid mixture comprising a hydrocarbon and a hydroperoxide corresponding to the hydrocarbon;
(2II) forming a second vapor/liquid mixture stream and a second liquid stream by passing the first liquid mixture through a first thin-film evaporation device under a first absolute pressure of at most 80 kPa;
(2III) separating the second vapor/liquid mixture stream in a first separation zone under a second absolute pressure of at most 80 kPa to obtain a third liquid stream and a third vapor stream;
(2IV) condensing a part of the third vapor stream at a location inside the first separation zone to obtain a fourth liquid stream and a fourth vapor stream;
(2V) recycling at least a part of the second, third, and fourth liquid streams to the first thin-film evaporation device;

(2VI) condensing a part of the fourth vapor stream at a location outside of the first separation zone to obtain a fifth liquid stream and a fifth vapor stream;

(2VII) obtaining the organic hydroperoxide product from the third liquid stream and/or the second liquid stream, wherein the organic hydroperoxide product has a higher concentration of the hydroperoxide compared to the first liquid mixture.

23. The process of claim 22, wherein the first liquid mixture comprises at most 25 wt % of the hydroperoxide, based on the total weight of the first liquid mixture.

24. The process of claim 22, wherein the organic hydroperoxide product comprises from 40 wt % to 95 wt % of the hydroperoxide, based on the total weight of the organic hydroperoxide product.

* * * * *